United States Patent [19]

Hutson, Jr.

[11] Patent Number: 4,528,411

[45] Date of Patent: Jul. 9, 1985

[54] DIESEL FUEL AND GASOLINE PRODUCTION

[75] Inventor: Thomas Hutson, Jr., Bartlesville, Okla.

[73] Assignee: Phillips Petroleum Company, Bartlesville, Okla.

[21] Appl. No.: 423,388

[22] Filed: Sep. 24, 1982

[51] Int. Cl.[3] ................................................ C07C 1/00

[52] U.S. Cl. .................................... 585/329; 585/330; 585/254; 585/517; 585/518; 585/520

[58] Field of Search ............... 585/329, 330, 254, 517, 585/518, 520

[56] References Cited

U.S. PATENT DOCUMENTS

| | | | |
|---|---|---|---|
| 2,564,964 | 8/1951 | Engle | 585/252 |
| 3,275,707 | 9/1966 | Bauer | 585/529 |
| 3,670,044 | 6/1972 | Drehman et al. | 585/433 |
| 3,697,615 | 10/1972 | Hughes | 585/277 |
| 4,005,985 | 2/1977 | Hutson, Jr. | 422/217 |
| 4,270,929 | 6/1981 | Dang Vu et al. | 44/56 |

*Primary Examiner*—Curtis R. Davis

[57] ABSTRACT

Process for producing high quality gasoline and diesel fuel from $C_3$ and $C_4$ olefinic cuts, such as those obtained by dehydrogenation of lower alkanes, comprising the steps of (a) polymerizing a $C_3$ olefinic cut to obtain a polymer gasoline fraction, (b) reacting a $C_4$ olefinic cut with an alkanol such as methanol to form methyltertiarybutyl ether and unreacted $C_4$ hydrocarbons, and (c) quenching the polymerization reaction in (a) with the unreacted $C_4$ hydrocarbons obtained in (b). The polymer gasoline fraction in (a) can be subjected to fractionation and hydrogenation to obtain additional streams for recycle and diesel fuel product.

14 Claims, 1 Drawing Figure

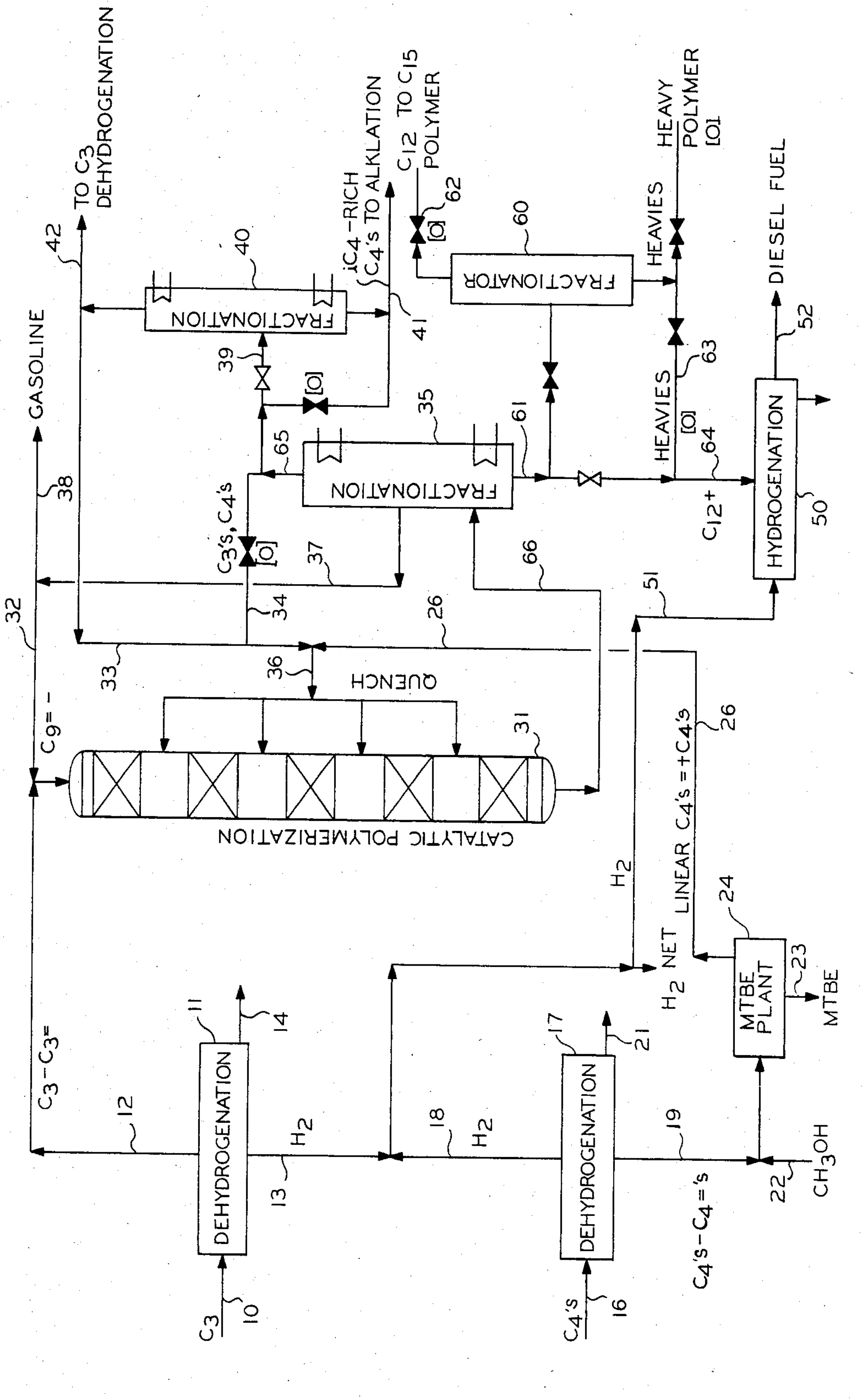
DEHYDROGENATION
DEHYDROGENATION
CATALYTIC POLYMERIZATION
QUENCH
FRACTIONATION
FRACTIONATION
FRACTIONATOR
HYDROGENATION
MTBE PLANT
MTBE
GASOLINE
TO C3 DEHYDROGENATION
iC4-RICH C4's TO ALKLATION
C12 TO C15 POLYMER
HEAVY POLYMER [O]
HEAVIES
HEAVIES [O]
DIESEL FUEL
C12+
C3's, C4's
C9=-
C3-C3=
C3
C4's
C4's-C4='s
CH3OH
H2
NET H2
LINEAR C4's=+C4's
10
11
12
13
14
16
17
18
19
21
22
23
24
26
31
32
33
34
35
36
37
38
39
40
41
42
50
51
52
60
61
62
63
64
65
66

DIESEL FUEL AND GASOLINE PRODUCTION

This invention relates to the production of diesel fuel and gasoline in a combination process. In another aspect, this invention relates to a combination process comprising polymerization and etherification together with appropriate fractionation for the production of polymer gasoline and disel fuel. In accordance with a further aspect, this invention relates to a combination process comprising polymerization and etherification wherein unreacted $C_4$ olefinic hydrocarbons from the etherification process are used to quench the polymerization process and yield additional olefin polymer. In accordance with a still further aspect, this invention relates to a combination type process including interrelationships of various streams from (a) propane and butane (mainly isobutane) separate dehydrogenations, (b) propylene catalytic polymerization, (c) methyltertiarybutyl ether manufacture, (d) various fractionations, and (e) hydrogenation of the heavier propylene polymer. In accordance with another aspect, this invention relates to a combination process for producing high quality diesel fuel and high quality gasoline from propane and butanes comprising polymerization and etherification wherein the unreacted linear $C_4$ olefin containing stream recovered from the etherification is used as at least part of the quench for olefin polymerization to cool the polymerization reaction and produce additional olefin polymer.

BACKGROUND OF THE INVENTION

Catalytic polymerization can be used to upgrade light olefins into gasolines of relatively high octane values and low vapor pressure providing an attractive process addition to a refinery. For example, low boiling olefins such as those containing from 3 to 5 carbon atoms per molecule can be effectively polymerized in the presence of various catalysts to produce copolymers, dimers, trimers, tetramers, etc. If desired, the products of such a polymerization can be hydrogenated to produce diesel fuels. It is also known to react isoolefins such as present in $C_4$ fractions and methanol in the presence of an acid catalyst to produce ethers such as methyltertiarybutyl ether, which is a known octane improver. Suitable olefinic feeds for the polymerization and etherification reaction can be obtained by dehydrogenation of $C_3$ and $C_4$ alkanes, respectively.

Catalytic polymerization is a highly exothermic reaction and heat removal considerations are important in order to produce desirable products. Such is the case experienced during the polymerization of low boiling olefins in the production of dimers, trimers, and tetramers. Various expedients have been attempted in an effort to control the polymerization reaction temperature. The present invention is directed to a combination process comprising polymerization and etherification for producing high quality diesel fuel and high quality gasoline from low boiling olefins wherein unreacted linear olefins recovered from the etherification reaction are used as at least part of the quench for the olefin polymerization to cool the reaction and produce additional linear olefin polymer.

Accordingly, an object of this invention is to produce high quality diesel fuel and high quality gasoline from low boiling olefins.

Another object of this invention is to provide a combination process for the polymerization and etherification of low boiling olefins.

Another object of this invention is to control polymerization reaction temperatures.

A further object of this invention is to provide a quench stream for olefin polymerization, to cool the polymerization reaction and produce additional polymer.

Other objects, aspects, as well as the several advantages of the invention will be apparent to those skilled in the art upon consideration of the specification, the drawing, and the appended claims.

SUMMARY OF THE INVENTION

Thus, according to the invention, there is provided a combination polymerization and etherification process comprising subjecting separate olefin-containing hyrocarbon feedstocks to polymerization and to etherification and utilizing at least a portion of the unreacted olefins from the etherification as quench for the polymerization to cool the polymerization reaction and form additional olefin polymer.

In accordance with one specific embodiment of the invention, the process comprises catalytically polymerizing propylene, such as obtained from propane dehydrogenation, to produce $C_{12}$ olefins, reacting olefins, such as butylenes as obtained from butanes dehydrogenation, with methanol to produce methyltertiarybutyl ether, passing at least portion of the unreacted linear butylenes removed from said ether production and passing same as a quench-reactant to the polymerization reaction, fractionating the polymer product and recycling a portion of the unreacted propylene and/or linear butylenes as quench-reactant to the polymerization reaction, and hydrogenating at least a portion of a $C_{12}$ olefins cut, after removal of heavies, to yield diesel fuel.

In accordance with another specific embodiment, the invention is a combination-type process including interrelationships of various streams from (a) propane and butane (mainly isobutane) separate dehydrogenations; (b) propylene catalytic polymerization; (c) methyltertiarybutyl ether manufacture; (d) various fractionations; (e) hydrogenation of the heavier propylene polymers; and (f) HF alkylation.

DETAILED DESCRIPTION

In actual operation of the invention according to a presently preferred embodiment, the invention is directed to a combination process for producing upgraded products from propane and butanes, wherein the butanes are dehydrogenated to butylenes, and the isobutylene is reacted therefrom with methanol conventionally to produce methyltertiarybutyl ether which is an octane improver for gasoline motor fuel. The propane is dehydrogenated to propylene which is conventionally polymerized to, in particular, recover a polymer which can be hydrogenated (using hydrogen from the dehydrogenation steps) to produce high Cetane Index diesel fuel. The unreacted linear butylenes-containing stream recovered from the MTBE is used as at least part of the quench between the multistage propylene (exothermic) catalytic polymerization, the linear butylenes therein also, in part, entering the polymerization reaction to produce linear olefin polymer which, after removal of light and heavy portions, is hydrogenated to high quality diesel fuel. If desired, some of the polymer can be recovered as product for other usage (e.g. detergent manufacture).

The lighter components from polymerization, especially the butanes-butylene cut which contains isobutane charged with the butanes feed as well as linear butylenes (and normal butane), are charged to such an HF alkylation to produce high octane gasoline.

An intermediate cut comprising nonenes and lighter (gasoline boiling range) is recovered as gasoline, and can, in part, be recycled to propylene polymerization to produce the higher boiling linear olefin to be hydrogenated to diesel fuel.

Optionally, at least some of the unreacted propylene-propane stream and butylenes-butane stream from product fractionation can be recycled to the polymerization and/or the propane-propylene stream can be recycled to dehydrogenation.

The invention is a flexible system of producing high quality diesel fuel and high quality gasoline, selecting the flow to the operations depending upon demand for diesel fuel and gasoline, as well as producing the MTBE octane improver from low quality propane and butanes feed materials.

Various stream flow arrangements are illustrated on the drawing to show the flexibility of the operation for producing diesel fuel and gasoline.

A paraffin hydrocarbon feed, for example, propane is passed to dehydrogenation zone 11 by way of line 10. The paraffinic feed is subjected to conventional dehydrogenation conditions in a thermal or catalytic dehydrogenation zone to convert the paraffin to an olefinic product removed from dehydrogenation zone by way of line 12. Hydrogen produced during dehydrogenation is removed by line 13 and unusable gaseous products by way of line 14.

A paraffinic hydrocarbon feed in line 16, for example, butanes is introduced into dehydrogenation 17 for the dehydrogenation of the butanes feed to form butylenes removed by line 19 and produced hydrogen is removed by line 18 and unusable gaseous materials by way of line 21.

The process conditions obtaining in dehydrogenation zones 11 and 17 are typical with temperatures being between about 950° and about 115° F., generally between about 1000° to 1100° F., and a total pressure in the range of 0 to 200 psig.

The butylenes-containing stream 19 is combined with methanol or other lower alkanol introduced by line 22 and the mixed feed is passed to etherification unit 24 wherein the reactants are converted to methyltertiarybutyl ether recovered in line 23 and unreacted linear butylenes removed by line 26.

The reaction between the $C_4$ cut and methanol is generally performed in the presence of an acid catalyst. The usual operating conditions are a temperature from about 0° to about 65° C. more often from about 10° to about 38° C. The etherification reaction is well-known.

Stream 12, which comprises an olefin-containing hydrocarbon poly feedstock, for example, propylene, is passed to catalytic polymerization reactor 31. In polymerization reactor 31 the feedstock contacts a bed of suitable polymerization catalyst such as phosphoric acid on a suitable support. The catalyst bed can be one continuous bed or is preferably divided into a plurality of beds as shown. While the catalyst beds are shown as being equal in size, it is within the scope of the invention to vary the volume or size of the individual catalyst beds. Polymerization reaction which takes place is highly exothermic and it is necessary to remove the heat evolved during the reaction in order to avoid undesirable side reactions.

In accordance with the invention, heat of reaction in polymerization reactor 31 is controlled by introducing unreacted linear $C_4$s removed from the etherification unit 24 into polymerization reactor 31 by way of lines 26 and 36. As shown in the drawing, a linear $C_4$ stream is used as quench for the polymerization reactor 31 and is introduced at spaced intermediate points of the reactor. When employing a plurality of beds as shown in the drawing, quenching can be done by introducing the linear $C_4$s as coolant between the beds and at the same time the linear $C_4$s are converted to dimers, trimers, and tetramers in the subsequent beds, to form additional olefin polymer, thereby increasing the overall yield of olefin polymer. The amount of quench introduced through each of the conduits into polymerization reactor 31 can be controlled by means of valves (not shown) in the conduit so as to maintain a substantially uniform temperature throughout the catalyst bed.

The reaction mixture removed from polymerization reactor 31 comprising olefin polymer and some unreacted olefins and saturated hydrocarbons is withdrawn by way of line 66 and introduced into fractionation zone 35 wherein the reaction mixture is subjected to suitable fractionation conditions to remove overhead a light fraction comprising $C_3$s and $C_4$s, an intermediate fraction comprising $C_9$s and lighter (gasoline boiling range), and a heavy olefin polymer (gasoline) product comprising $C_{12}$s and heavier. The light overhead fraction in line 65 comprising $C_3$s and $C_4$s can be, if desired, passed by way of lines 34 and 36 as part of the quench-reactant to polymerization reactor 31 or part or all sent to further fractionation by way of line 39 and introduced into fractionation zone 40. The $C_3$s and $C_4$s feed is subjected to fractionation conditions in zone 40 to remove $C_3$s overhead by line 42 which, in part, can be passed to dehydrogenation, for example zone 11, and the remainder returned via lines 33 and 36 as part of the quench-reactant to polymerization reactor 31.

A bottoms steam comprising $C_4$s is removed from fractionaton 40 and passed via 41 to conventional alkylation. The alkylation zone (not shown) can be conducted under conventional conditions for aliphatic alkylation. Known catalysts for the reaction of isobutane with butenes can be used, hydrofluoric acid being preferred. Other catalysts are sulfuric acid, phosphoric acid, and the like.

If desired, a portion or all of the $C_3$s and $C_4$s in line 39 can bypass fractionation zone 40 and be sent directly by way of line 41 to alkylation.

An intermediate fraction comprising $C_9$s and lighter (gasoline boiling range) stream removed by line 37 from fractionation 35 can either pass through line 38 as gasoline product or returned in part or in toto by way of line 32 to polymerization reactor 31.

A heavy olefin polymer stream comprising $C_{12}$s and heavier is removed from a lower portion of fractionation zone 35 and either passed by way of line 61 to fractionation zone 60 or by way of line 64 to hydrogenation zone 50. If the heavy olefin polymer stream is passed to fractionation zone 60, it is subjected to fractionation conditions so as to remove overhead by way of line 62, a product stream comprising $C_{12}$–$C_{15}$ polymer and a heavies stream as bottoms. The heavy stream removed from fractionation 60 can be yielded as heavy polymer, if desired, or passed by way of line 63 and introduced along with material in line 64 to hydrogenation 50. The olefin polymer feed to zone 50 is subjected to hydrogenation conditions in the presence of hydrogen introduced by way of line 51 to form a saturated product which is yielded as diesel fuel by way of line 52. The hydrogenation reaction can take place in a suitable reaction zone at a temperature in the range of from about 0° C. to about 150° C. The amount of hydrogen employed is in the range of from about 0.1 to about 100 moles of hydrogen per mole of double bond equivalent olefin feed. Reaction pressure can range from about 100 to about 1000 psig. Nickel on kieselguhr is a typical catalyst.

The following calculated example serves to further illustrate the invention.

EXAMPLE

In this example typical operating conditions and units as illustrated in the drawing are set forth. The stream unit numbers in the example correspond to identical unit numbers in the drawing.

| Operation of Units | | |
|---|---|---|
| Unit (11), Propane Dehydrogenaton: | | |
| Catalyst: Platinum—Tin on $ZnAl_2O_4$[(a)] 0.6 wt. % Pt; 0.1 wt. % Sn | | |
| Feed (10): | | |
| Propane, bbl/day | | 25,473 |
| Yields (12): | | |
| Propane, bbl/day | | 18,000 |
| Propylene, bbl/day | | 7,200 |
| | Total | 25,200 |
| Yield (13): | | |
| Hydrogen, millions scf/day | | 15.35 |
| Yield (14): | | |
| Gaseous Waste, mlbs/day | | 176.03 |
| Liquid Hourly Space Velocity, | | |
| Volumes/vol. cat/hr., | | 4.0 |
| Temperature, °F., | | 1100 |
| Pressure, psig, | | 55 |

[(a)]Can use any conventional propane dehydrogenation.

| Unit (17), Butanes Dehydrogenation: | | |
|---|---|---|
| Catalyst: Pt—Sn on $ZnAl_2O_4$[(b)] 0.6 wt. % Pt; 0.1 wt. % Sn | | |
| Feed (16): | | |
| Normal Butane, bbl/day | | 1,000 |
| Isobutane, bbl/day | | 49,949 |
| Yield (19): | | |
| Normal Butane, bbl/day | | 500 |
| Isobutane, bbl/day | | 24,975 |
| Isobutylene, bbl/day | | 22,478 |
| n-Butenes, bbl/day | | 450 |
| | Total | 48,403 |
| Yield (18): | | |
| Hydrogen, million scf/day | | 19.42 |
| Yield (21): | | |
| Gaseous waste, mlbs/day | | 406.9 |
| Liquid Hourly Space Velocity | | |
| Vol/vol cat/hr | | 4.0 |
| Temperature, °F. | | 1050 |
| Pressure, psig. | | 55 |

[(b)]Can use any conventional butanes dehydrogenation.

| Unit (24) MTBE Manufacture: | |
|---|---|
| Feed Methanol (22), bbl/day | 9,709 |
| Feed Butylenes (19), bbl/day (see above) | 48,403 |

-continued

| Unit (24) MTBE Manufacture: | |
|---|---|
| Vol. % Isobutylene | 46.44 |
| MTBE Product (23), bbl/day | 27,428 |
| Linear Olefins (26), bbl/day (includes, $iC_4$, $nC_4$, $nC_4=$/s) | 25,925 |
| Catalyst: Amberlyst - 15 (Conventional) | |
| Weight Hourly Space Velocity, lb/lb cat/hr | 2.8 |
| Temperature, °F., | 155 |
| Pressure, psia, | 180 |

| Unit (31) Catalytic Polymerization (conventional): | |
|---|---|
| Feed propylene (12) (see above), b/d | 25,200 |
| Recycle $C_9$ - Olefins (32), bbl/day | 50,904 |
| Recycle Propylene (33), bbl/day (optional) (Vol % Propylene 2.8) | 250 |
| Linear Olefins (26) from MTBE, bbl/day | 25,925 |
| Recycle $C_3$, $C_4$ olefins (34), b/d (optional) | 250 |
| Total Recycle (36), b/d | 77,329 |
| Catalyst: Phosphoric Acid on Kieselguhr (conventional) | |
| Liquid Hourly Space Velocity, Vol total feed/vol cat/hr | 1.15 |
| Pressure, psia. | 600 |
| Temperature, °F. | 420 |
| Conventional Fractionation (35):[(c)] | |
| Overhead (65), b/d | 43,835 |
| Recycle (34), b/d (see above) (optional) | 0 |
| Feed to Depropanizer (40) via (39), b/d | 43,835 |
| Recycle (32), b/d (see above) | 52,635 |
| Gasoline Yield (38), b/d | 1,731 |
| Conventional Fractionation (40):[(d)] | |
| Feed (39), b/d (see above) | 43,835 |
| Recycle Overhead (33), b/d (see above) | 250 |
| Overhead Yield b/d (42), Vol % Propylene, 0.6 | 17,910 |
| Bottoms Yield (41), b/d Vol % $nC_4$ = 's, 0.03 | 25,925 |
| Conventional Fractionation (60):[(e)] | |
| Feed (61), b/d | 5,168 |
| $C_{12-15}$ Polymer (62), b/d [5,064 (optional)] | 0 |
| Heavy Polymer (63), b/d [104 (optional)] | 0 |
| Conventional Hydrogenation Unit (50): | |
| Polymer Feed (64), bbl/day | 5,168 |
| Hydrogen (51), million scf/day | 5.17 |
| Diesel Fuel (52), bbl/day | 5,374 |

[(c)]Can be $DC_3$ column and $DeC_4$ column.
[(d)]$C_3$-$C_4$ splitter.
[(e)]Deoiler (not used in example).

The invention advantageously upgrades low value propane and butanes to high octane olefin gasoline, methyltertiarybutyl ether (MTBE) and high Cetane Index diesel fuel. The system is flexible in producing more or less gasoline and less or more diesel fuel, depending upon sales demands of these two products. The unreacted linear butylenes from MTBE are used not only to quench the staged catalytic polymerization where conventionally propane is used as quench, but the linear butylenes produce additional high boiling olefin product for gasoline and/or diesel fuel.

I claim:

1. A combination process for producing high quality diesel fuel and high quality gasoline which comprises the steps of (a) polymerizing an olefinic $C_3$ cut comprising propylene in a polymerization zone containing a polymerization catalyst active for catalyzing polymerization of said olefins to linear olefin polymers boiling within the gasoline boiling range, (b) contacting a mixture of methanol and an olefinic $C_4$ cut comprising isobutene, isobutane, and at least one n-butene with an acid catalyst under isobutene etherification conditions to produce methyltertiarybutyl ether and unreacted linear $C_4$ hydrocarbons, and (c) introducing at least a portion of said unreacted linear $C_4$ hydrocarbons in (b) into said polymerization zone in (a) as quench to cool the polymer reaction and produce additional linear olefin polymer from linear $C_4$ olefin hydrocarbons in said at least a portion of said unreacted linear $C_4$ hydrocarbons in the presence of said propylene in (a).

2. A process according to claim 1 wherein the olefinic feed for said polymerization in (a) and the olefinic feed for said etherification in (b) are obtained by separate dehydrogenation of propane and butanes, respectively.

3. A process according to claim 1 wherein said polymerization zone in (a) is a multi-stage polymerization zone which contains a plurality of beds of polymerization catalyst in spaced relationship with one another between the inlet and outlet of said zone.

4. A process according to claim 3 wherein said unreacted $C_4$ hydrocarbons in (c) are introduced as quench into said polymerization zone between at least two of the spaced catalyst beds.

5. A process according to claim 1 wherein the effluent from said polymerization zone in (a) is passed to fractionation to recover a light overhead fraction comprising $C_3$ and $C_4$s, an intermediate fraction comprising $C_9$s and lighter (gasoline boiling range) and a heavy olefin polymer product comprising $C_{12}$s and heavier.

6. A process according to claim 5 wherein said heavy olefin polymer product is divided into a first portion which is recovered as polymer gasoline product and into a second portion which is subjected to hydrogenation to form high quality diesel fuel.

7. A process according to claim 5 wherein at least a portion of said light overhead fraction is returned as part of the quench (a) and at least another portion is passed to further fractionation to recover $C_4$s for alkylation and $C_3$s for dehydrogenation.

8. A process according to claim 5 wherein at least a portion of said intermediate fraction is returned as part of the feed for said polymerization in (a) and at least another portion is recovered as high quality gasoline product.

9. A process according to claim 6 wherein said first portion is subjected to further fractionation to obtain an overhead $C_{12}$–$C_{15}$ polymer stream and a bottoms heavy polymer stream.

10. A process according to claim 2 wherein the effluent from said polymerization zone in (a) is passed to fractionation to recover a light overhead fraction comprising $C_3$ and $C_4$s, an intermediate fraction comprising $C_9$s and lighter (gasoline boiling range), and a heavy olefin polymer product comprising $C_{12}$s and heavier, and further wherein said heavy olefin polymer product is divided into a first portion which is recovered as a polymer product and into a second portion which is subjected to hydrogenation to form high quality diesel fuel.

11. A process according to claim 10 wherein at least a portion of said light overhead fraction is returned as part of the quench in (a) and at least another portion is passed to further fractionation to recover $C_4$s for alkylation and $C_3$s for dehydrogenation.

12. A process according to claim 10 wherein at least a portion of said intermediate fraction is returned as part of the feed for said polymerization in (a) and at least another portion is recovered as high quality gasoline product.

13. A process according to claim 10 wherein said first portion is subjected to further fractionation to obtain an overhead $C_{12}$–$C_{15}$ polymer stream and a bottoms heavy polymer stream.

14. A process according to claim 1 wherein said olefinic feed for said polymerization in (a) and said olefinic feed for said etherification in (b) are obtained by seperate dehydrogenation of propane and butanes, respectively, and further wherein said polymerization zone in (a) is a multi-stage polymerization zone which contains a plurality of beds of polymerization catalysts in spaced relationship with one another between the inlet and outlet of said zone, and further wherein said unreacted $C_4$ hydrocarbons in (c) are introduced as quench into said polymerization zone between at least two of the spaced catalyst beds.

* * * * *